(12) United States Patent
Di Naro

(10) Patent No.: US 11,959,913 B2
(45) Date of Patent: Apr. 16, 2024

(54) QUANTITATIVE CELLULAR METHOD FOR DETERMINING THE BIOLOGICAL ACTIVITY OF AN ANTI-CD26 LIGAND

(71) Applicant: ADIENNE S.A., Lugano (CH)

(72) Inventor: Antonio Francesco Di Naro, Morcote (CH)

(73) Assignee: ADIENNE S.A., Lugano (CH)

(*) Notice: Subject to any disclaimer, the term of this patent is extended or adjusted under 35 U.S.C. 154(b) by 605 days.

(21) Appl. No.: 16/768,206

(22) PCT Filed: Dec. 21, 2018

(86) PCT No.: PCT/IB2018/060507
§ 371 (c)(1),
(2) Date: May 29, 2020

(87) PCT Pub. No.: WO2019/123410
PCT Pub. Date: Jun. 27, 2019

(65) Prior Publication Data
US 2020/0319169 A1   Oct. 8, 2020

(30) Foreign Application Priority Data

Dec. 22, 2017 (IT) .................. 102017000148959

(51) Int. Cl.
| | |
|---|---|
| G01N 33/533 | (2006.01) |
| C07K 16/28 | (2006.01) |
| G01N 33/50 | (2006.01) |
| G06F 17/18 | (2006.01) |
| C07K 16/40 | (2006.01) |

(52) U.S. Cl.
CPC ......... G01N 33/533 (2013.01); G01N 33/505 (2013.01); G06F 17/18 (2013.01); C07K 16/2896 (2013.01); C07K 16/40 (2013.01); G01N 2333/70596 (2013.01)

(58) Field of Classification Search
CPC .... G01N 33/533; G01N 33/505; G06F 17/18; C07K 16/2896
See application file for complete search history.

(56) References Cited

U.S. PATENT DOCUMENTS 9,376,498 B2   6/2016   Di Naro

FOREIGN PATENT DOCUMENTS

WO   WO-02092127 A1 * 11/2002 ............. A61K 38/19

OTHER PUBLICATIONS

Kohiji yamada et al. Localization of CD26/DPPIV in nucleus and its nuclear translocation enhanced by anti-CD26 monoclonal antibody with anti-tumor effect. Cancer Cell International, 9, 17. (Year: 2009).*

Philip Riz et al. Cytofluorographic Evidence That Thymocyte Dipeptidyl Peptidase IV (CD26) Activity Is Altered With Stage of Ontogeny and Apoptotic Status. Cytometry, 23, 322-329. (Year: 1996).*
Andrea Bacigalupo et al., Treatment of Patients with Steroid Refractory Acute Graft Vs Host Disease (SR-GvHD): A Matched Paired Analysis of Anti-CD26 (Begelomab) compared to other treatment, Blood, 22, 671. (Year: 2016).*
T. Mattern et al., Antibody-induced modulation of CD26 surface expression, Immunology, 84, 595-600. (Year: 1995).*
Natasha Kekre et al., Emerging drugs for graft-versus-host disease, Expert Opinion on Emerging Drugs, 21(2), 209-218. (Year: 2016).*
Nina Koliha et al. A novel multiplex bead-based platform high lights the diversity of extracellular vesicles, J Extracellular Vesicles,5, 29975. (Year: 2016).*
Elizabeth Crabb Breen et al. Multisite Comparison of High-Sensitivity Multiplex Cytokine Assays, Clinical and Vaccine Immunology, 1229-1242. (Year: 2011).*
Abbott, C.A., et al., "Genomic organization, exact localization, and tissue expression of the human CD26 (dipeptidyl peptidase IV) gene," *Immunogenetics* 40(5):331-338, Springer Verlag, Germany (1994).
Bacigalupo, A., et al., "Treatment of Patients with Steroid Refractory Acute Graft Vs Host Disease (SR-GvHD): A Matched Paired Analysis of Anti-CD26 (Begelomab) Compared to Other Treatment," *Blood* 128(22): Abstract #671, American Society of Hematology, United States (Dec. 2016).
Cordero, O.J., et al., "On the role of CD26 in CD4 memory T cells," *Immunobiology* 212(2):85-94, Elsevier, Netherlands (2007).
De Meester, I., et al., "CD26, let it cut or cut it down," *Immunol Today* 20(8):367-375, Elsevier, Netherlands (1999).
Ferrara, J.L.M., et al., "Graft-versus-host disease," *Lancet* 373(9674): 1550-1561, Elsevier Ltd., United Kingdom (2009).
Franco, R., et al., "Enzymatic and extraenzymatic role of ecto-adenosine deaminase in lymphocytes," *Immunological Reviews* 161(1):27-42, Wiley-Blackwell Publishing Ltd., United Kingdom (1998).
Gorrell, M.D., et al., "CD26: a multifunctional integral membrane and secreted protein of activated lymphocytes," *Scandinavian Journal of Immunology* 54(3):249-264, Wiley-Blackwell Publishing Ltd., United Kingdom (2001).
Hatano, R., et al., "Prevention of acute graft-versus-host disease by humanized anti-CD26 monoclonal antibody," *British Journal of Haematology* 162(2):263-277, Wiley-Blackwell Publishing Ltd., United Kingdom (2013).
Henden, A.S., and Hill, G.R., "Cytokines in Graft-versus-Host Disease," *Journal of Immunology* 194(10):4604-4612, American Association of Immunologists, United States (2015).
Hildebrandt, M., et al., "A guardian angel: the involvement of dipeptidyl peptidase IV in psychoneuroendocrine function, nutrition and immune defence," *Clinical Science (Lond)* 99(2):93-104, Portland Press, United Kingdom (2000).

(Continued)

*Primary Examiner* — Michael G. Hartley
*Assistant Examiner* — Jagadishwar R Samala
(74) *Attorney, Agent, or Firm* — Sterne, Kessler, Goldstein & Fox P.L.L.C.

(57) ABSTRACT

The present invention relates to a quantitative cellular method for the in vitro determination of the effect of an anti-CD26 ligand, preferably of an anti-CD26 monoclonal antibody, such as begelomab.

12 Claims, 13 Drawing Sheets

(56) References Cited

OTHER PUBLICATIONS

Klemann, C., et al., "Cut to the chase: a review of CD26/dipeptidyl peptidase-4's (DPP4) entanglement in the immune system," *Clinical and Experimental Immunology* 185(1):1-21, Wiley-Blackwell Publishing Ltd., United Kingdom (2016).

Morimoto, C., et al., "1F7, a novel cell surface molecule, involved in helper function of CD4 cells," *Journal of Immunology* 143(11):3430-3439, American Association of Immunologists, United States (1989).

Morimoto, C., and Schlossman, S.F., "The structure and function of CD26 in the T-cell immune response," *Immunological Reviews* 161(1):55-70, Wiley-Blackwell Publishing Ltd., United Kingdom (1998).

Mattern, T., et al., "Expression of CD26 (Dipeptidyl Peptidase IV) on Resting and Activated Human T-Lymphocytes," *Scandinavian Journal of Immunology* 33(6):737-748, Wiley-Blackwell Publishing Ltd., United Kingdom (1991).

Ohnuma, K., et al., "Dipeptidyl peptidase in autoimmune pathophysiology," *Advances in Clinical Chemistry* 53(1):51-84, Academic Press Inc., United States (2011).

Sauer, A.V., et al., "Autoimmune dysregulation and purine metabolism in adenosine deaminase deficiency," *Frontiers in Immunology* 3:265, Frontiers Media S.A., Switzerland (2012).

Seidel, U.J.E., et al., "Natural killer cell mediated antibody-dependent cellular cytotoxicity in tumor immunotherapy with therapeutic antibodies," *Frontiers in Immunology* 4:76, Frontiers Media S.A., Switzerland (2013).

Shaikh, P.Z., "Cytokines & their physiologic and pharmacologic functions in inflammation: A review," *International Journal of Pharmacy & Life Sciences* 2(11):1247-1263, Sakun Publishing House, India (2011).

Vacaflores, A., et al., "Exposure of Human CD4 T Cells to IL-12 Results in Enhanced TCR-Induced Cytokine Production, Altered TCR Signaling, and Increased Oxidative Metabolism," *PLoS One* 11(6):e0157175, Public Library of Science, United States (2016).

Welniak, L.A., et al., "Immunobiology of allogeneic hematopoietic stem cell transplantation," *Annual Review of Immunology* 25:139-170, Annual Reviews Inc., United States (2007).

Yi, T., et al., "Reciprocal differentiation and tissue-specific pathogenesis of Th1, Th2, and Th17 cells in graft-versus-host disease," *Blood* 114(14):3101-3112, American Society of Hematology, United States (2009).

Herrera, C., et al., "Comodulation of CXCR4 and CD26 in human lymphocytes," J Biol Chem 276(22):19532-19539, American Society for Biochemistry and Molecular Biology, United States (Jun. 2001).

Ho, L., et al., "In vitro and in vivo antitumor effect of the anti-CD26 monoclonal antibody 1F7 on human CD30+ anaplastic large cell T-cell lymphoma Karpas 299," Clin Cancer Res 7(7):2031-2040, American Association for Cancer Research, United States (Jul. 2001).

Yamada, K., et al., "Nuclear localization of CD26 induced by a humanized monoclonal antibody inhibits tumor cell growth by modulating of POLR2A transcription," PLoS One 8(4):e62304, PLoS, United States (Apr. 2013).

\* cited by examiner

QUANTITATIVE CELLULAR METHOD FOR DETERMINING THE BIOLOGICAL ACTIVITY OF AN ANTI-CD26 LIGAND

CROSS-REFERENCE TO RELATED APPLICATIONS

This application is a U.S. national stage filing of International Application No. PCT/IB2018/060507, filed Dec. 21, 2018; which claims priority to IT Application No. 102017000148959, filed Dec. 22, 2017. The entire contents of International Application No. PCT/IB2018/060507 are hereby incorporated herein by reference.

The present invention relates to a quantitative cellular method for the in vitro determination of the effect of an anti-CD26 ligand, preferably of an anti-CD26 monoclonal antibody, such as begelomab.

CD26 is a 110-kDa multifunctional glycoprotein expressed both on the cell surface and in soluble form. The CD26 antigen is expressed by various tissues and organs such as the lungs, endothelium, heart, brain, liver, intestine, kidneys, placenta, pancreas and skeletal muscles (Abbott C. A. et al., 1994). At the cellular level, the expression of CD26 has been found to have a strong co-stimulatory activity in lymphocyte populations, specifically in activated T lymphocytes, in T resting and on B lymphocytes (Cordero O J et al., 2007). On a specific subset of memory T cells, in fact, the expression of CD26 increases following activation of the T cells themselves (Morimoto C. et al., 1989). The expression of CD26 on T cells has been associated with the ability of these cells to produce high amounts of IL-2 and strongly proliferate in response to mitogenic stimulation. The expression of CD26, however, has been negatively correlated with the activity of T-helper lymphocytes (Mattern T. et al., 1991).

CD26 is characterized by a dipeptidyl peptidasic IV (DPP-IV) enzymatic activity. The above enzymatic activity specifically promotes the hydrolysis of the peptide bond between the N-terminal amino acid in X-Pro position and adjacent amino acids (Gorrel M. D. et al., 2001). CD26 belongs to a subset of oligopeptidases that can cut N-terminal dipeptides from many biologically active substrates such as cytokines, polypeptides, hormones and chemokines (De Meester I. et al, 1999; Hildebrandt M. et al., 2000).

In human beings, CD26 is also involved in binding with adenosine deaminase (ADA) (Franco R. et al., 1998). ADA deficiency predisposes to immunodeficiency diseases, not only through the general mechanisms of immune dysregulation, but also through the intracellular accumulation of toxic metabolites of the purine metabolism (Sauer A. V. et al., 2012).

A possible effect of the link between CD26 and ADA is in fact the modulation of the local extracellular adenosine concentration that gives negative signals within T cells through the adenosine receptors of the cell surface. Some monoclonal antibodies specific for CD26 are capable of transmitting an activation signal to T cells and regulating immune responses in vitro (Morimoto C. and Schlossman S. F et al, 1998). CD26 has therefore been associated with the regulation of inflammation, immune endocrine and nervous functions and also the pathophysiology of AIDS.

Due to its ubiquitous distribution, many pathological states are correlated to an altered expression and/or activity of CD26 in relation to the severity of the respective pathological condition. These diseases can be divided into at least five categories: autoimmune and inflammatory diseases, malignant hematological tumors, psychoneuroendocrine disorders, infectious diseases and solid tumors. Many researchers have observed that in various immune-mediated diseases, the serum level of enzymatic activity of CD26 appears to be altered (Klemann C. et al., 2016). In clinical studies, it has been observed that variations in the expression/activity of CD26 are involved in various autoimmune diseases such as rheumatoid arthritis, multiple sclerosis, type I diabetes mellitus and transplant rejection disease in the host (GvHD).

Various studies, in which highly selective CD26 inhibitors were administered, showed a delayed onset of diabetes, a decrease in insulitis, an increase in the number of regulatory T cells, suggesting an important role of CD26 in immune regulation.

Several reports relating to patients suffering from rheumatoid arthritis have shown a correlation between the CD26 expression/enzymatic activity, the severity of the disease and the treatment. These findings could pave the way for new therapeutic approaches aimed at inhibiting the enzymatic activity of CD26. Furthermore, the CD26 expression has been seen to be higher on the surface of T cells in the blood and cerebrospinal fluid of patients suffering from multiple sclerosis (Ohnuma K. et al., 2011). GvHD is the main complication following haematopoietic stem cell transplantation (HSCT), an important therapy for many haematological diseases (Ferrara J. L. M. et al., 2009). GvHD can be classified as acute or chronic based on the time of onset and is caused by the transplantation of naïve T cells deriving from the donor's marrow, which damage the recipient's tissue (Henden A. S., Hill G. R., 2015). GvHD represents a strict limitation on the use of bone marrow transplant as a life-saving therapy (Welniak L. A. et al., 2007).

Three conditions are generally necessary for the development of GvHD: (1) the donor's marrow must contain immunocompetent cells, (2) the recipient must express tissue antigens that are not present in the donor and (3) the recipient should not be able to trigger an effective response that would destroy the transplanted cells.

GvHD is characterized by 3 distinct phases: 1) in a first phase the tissues are damaged in the host due to radiotherapy and chemotherapy, with the release of pro-inflammatory cytokines, such as TNF-alpha and IFN-gamma; 2) in a second activation phase the allo-reactive T cells of the donor are activated by the antigens exposed by the cells presenting the antigen of the recipient (APC), 3) lastly the cell proliferation occurs with further secretion of cytokines produced by both cytotoxic T cells and the effector T cells (Ferrara J. L. M. et al., 2009).

The pathology, severity and organ-specificity of acute GvHD (aGvHD) is determined by the balance between the different subpopulations of T lymphocytes: Th1, Th2 and Th17. It has been shown, in fact, that the prevalence of the Th1 subtype with respect to the others depends on the cytokine environment at the time of activation of the T cells of the donor, following interaction with the APC cells of the host, and their subsequent differentiation into helper T cells.

The main Th1 cytokines are IFN-γ, IL-2 and TNF alpha. Increased amounts of Th1 cytokines, such as TNF and IFN-γ, have been associated with a more precocious and severe onset of the disease due to their capacity of inducing the up-regulation of chemokines and receptors capable of promoting an inflammatory reaction. Th2 cytokines are IL-4, IL-5, IL-10 and IL-13. It has been observed that the blocking of the response by Th2 cells is associated with an increase in gastrointestinal symptoms and a reduction in liver and skin damage levels. IL-6, which is a pro-inflammatory cytokine, controls the balance between Th17 cells and regulatory T cells. IL-6 inhibition could be a potentially effective strategy for reducing the severity of aGvHD in HCT through the induction of immunological tolerance (Henden A. S., Hill G. R., 2015).

Therefore, clarifying the role of CD26 during the response of T cells and altered levels of cytokines would undoubtedly help to understand the onset phenomenon and the progression of GvHD (Henden A. S., Hill G. R., 2015; Yi T. 2009).

On the basis of this premise, a new therapeutic approach for preventing the onset of GvHD is based on the use of anti-CD26 monoclonal antibodies (Hatano R., 2013; Bacigalupo A., 2016). Anti-CD26 antibodies have recently been developed in preclinical models to prevent the onset of GvHD in animal models of the disease.

Although the role of CD26/DPPIV in GvHD should be further investigated, treatment with a mouse antibody against human CD26 (i.e. Begelomab) has been reported to be effective in the treatment of GvHD in patients suffering from acute steroid-resistant GvHD (U.S. Pat. No. 9,376, 498). Clinical data therefore confirm that the inactivation of CD26 by a monoclonal antibody represents a valid therapeutic approach for eradicating the subpopulation of self-reactive T cells with the consequent resolution of GVHD.

In light of the above, the importance of the CD26 receptor as a molecular target in new therapeutic approaches is evident.

The potency test provides a quantitative measurement of the biological activity of a specific drug and represents a crucial quality parameter during the development process of a pharmacological molecule.

Various approaches can be used for developing a potency test, including ligand-receptor assays, animal assays, in vitro cell assays, or other biochemical assays (eg enzyme assays). A potency test is particularly relevant if it reproduces the action mechanism of a particular drug.

For biological products, it is preferable to use a ligand-receptor assay or in vitro cell experiments. The former, as it is able to provide a direct measurement of the affinity of the drug to its molecular target, can also be suitable for a potency test.

It is not always possible, however, to use these types of assays, simply because the potency tests should be developed based on the action mechanism of the drug, but this information is not always available, especially for monoclonal antibodies. This approach is particularly complex as biological drugs often have multiple action mechanisms in vivo, such as to be particularly difficult to reproduce in an in vitro system.

The authors of the present invention have now discovered that the anti-CD26 monoclonal antibody (begelomab) is able to induce the internalization of the CD26 receptor after binding specifically, with an mechanism of action known as "capping". The internalization phenomenon leads to the inhibition of the release of pro-inflammatory cytokines, which play a crucial role in phlogistic processes, which is a direct downstream functional event induced by the anti-CD26 ligand. The mechanism of action described thus supports all the applications of monoclonal antibodies in all autoimmune diseases in which it is essential to deactivate the self-reactive T lymphocytes while preserving their immunocompetence.

Consequently, as a potency test of a pharmaceutical product is generated for the purpose of determining the amount of active compound in a sample in a functional way, the internalization of CD26 and inhibition in the secretion of inflammatory cytokines both represent a new test that can be used for evaluating the potency of any anti-CD26 ligand, preferably a monoclonal antibody being developed for therapeutic and/or diagnostic applications.

The approach described can be applied in order to evaluate the potency of any anti-CD26 based on the revolutionary discovery of the mechanism of action of begelomab. Furthermore, the use of this method allows a quantitative measurement of both the internalization of CD26 and the inhibition of the secretion/production of cytokines to be obtained.

In conclusion, these findings allow the preparation of an extremely advantageous potency test in terms of 1) reproducibility, 2) ease of quantification of the activity of the anti-CD26 ligand in a specific sample, and 3) quantitative measurement of the activity of the anti-CD26 ligand, whether it be known as Begelomab or newly identified.

The present invention therefore relates to a method for the in vitro determination of the potency of an anti-CD26 ligand comprising the following steps:

a) incubation at 37° C. of a population of human T lymphocytes expressing the CD26 receptor in a percentage higher than 75% with an anti-CD26 ligand, at a concentration ranging from 0.001 μg/ml and 150 μg/ml; preferably from 0.01 μg/ml to 100 μg/ml, more preferably from 0.01 μg/ml to 2 μg/ml, even more preferably from 0.01 μg/ml to 0.5 μg/ml;

b) incubation with anti-CD26 antibody marked with fluorochrome that recognizes an epitope on the CD26 receptor different from that recognized by the anti-CD26 ligand of step a);

c) determination of the MFI value (Median of Fluorescence Intensity) of CD26 measured for the sample of cells treated with the anti-CD26 ligand ($MFI_T$) and the MFI value of non treated cells ($MFI_{NT}$) by means of cytofluorimetric analysis;

d) evaluation of the internalization percentage of the CD26 receptor as RFI (Relative fluorescence Intensity, that is MFI value normalized with respect to the basal) calculated as the ratio between the MFI value of CD26 measured for the sample of cells treated with the anti-CD26 ligand ($MFI_T$) and the MFI value of non treated cells ($MFI_{NT}$), multiplied by 100 and then subtracted from 100, according to the following formula:

$$RFI = \% \; int \; CD26 = 100 - \left(\frac{MFI_T}{MFI_{NT}} \times 100\right)$$

wherein "% int CD26" or RFI is the internalization percentage of CD26, "$MFI_T$" is the MFI value of cells treated with the CD26 ligand (test cells) and "$MFI_{NT}$" is the MFI value of the cells non treated with CD26 ligand (reference cells).

Such percentage (% int CD26 or RFI):

if less than 20% indicates a low potency of the anti-CD26 ligand;

if ranging from 20% to 30% indicates a medium potency of the anti-CD26 ligand;

if higher than 30% indicates a high potency of the anti-CD26 ligand.

In FIG. 12, panel A it is pointed out the rational employed to assign the criteria of "low", "medium" and "high" potency, respectively. In particular, it is observed that the response in terms of % of CD26 internalization is dose-dependent with S shape (sigmoidal), wherein at lower concentration of the ligand (in this figure indicated as "RS") it has lower "% int CD26" value and, viceversa, at greater concentration of the ligand it has greater "% int CD26" value until a maximum (plateau) of 30%-35%. If this plateau is considered as 100% of "% int CD26" it is possible to normalize all the values of the curve as shown in FIG. 12, panel B.

In this sense a curve starting from 0% to 100% of internalization is observed and thus, it is possible to define three different potency ranges:
1. "low", that is referred to a ligand having an internalization percentage ranging from 0% to 50% with respect to the plateau,
2. "medium", that is referred to a ligand having an internalization percentage ranging from 50% to 90% with respect to the plateau,
3. "high", that is referred to a ligand having an internalization percentage higher than 90% with respect to the plateau.

In other terms this concept may be summarized in the following Table 1:

TABLE 1

| Potency | RFI | % plateau |
|---|---|---|
| LOW | 0%-20% | 0%-50% |
| MEDIUM | 20%-30% | 50%-90% |
| HIGH | >30% | 90%-100% |

In an alternative embodiment of the invention, the population of human lymphocytes of step a) can be incubated at room temperature.

Said anti-CD26 ligand is any molecule capable of binding specifically to the CD26 receptor, preferably an anti-CD26 monoclonal antibody or fragments thereof, more preferably begelomab.

In a preferred embodiment of the method of the invention, the concentration of anti-CD26 ligand of step a) is 0.001 µg/ml, 0.01 µg/ml, 0.5 µg/ml or 2 µg/ml.

In a preferred embodiment of the method of the invention, the anti-CD26 antibody of step b) is of the type mouse anti-human CD26 APC fluorochrome-conjugated (BD Pharmingen; catalogue number: 563670, clone number: M-A261) and is incubated at a concentration of 2.5 µg/ml.

According to a further preferred embodiment of the method of the invention, the fluorochrome used in step b) is any fluorochrome that can be used for cytofluorimetric analysis selected from the group consisting of FITC, APC, PE, PE-Cy7, APC-H7, PerCP and PE-Cy5.5. Said fluorochrome is preferably APC.

Again, according to a preferred embodiment of the method of the invention, the population of CD26+ T lymphocytes of step a) is selected from a population of primary T lymphocytes and a tumor cell line of human T lymphocytes. Preferably, said tumor cell line of human T lymphocytes is the Karpas 299 cell line.

In a preferred embodiment of the method according to the invention, the cytofluorimetric analysis of step c) is carried out by means of FACS.

The method according to the invention also provides a further verification step of the potency of the anti-CD26 ligand which provides for an inhibition test of cytokine release by the above-mentioned ligand, said cytokines being selected from the group consisting of IL-8, IL-1β, IL-6, IL-2, GM-CSF, IL-6 and TNF-α effected on the population of CD26+ human T lymphocytes of step a). In a preferred embodiment, said cytokines are IL-8 and/or IL-1β. Said population of CD26+ human T lymphocytes of step a) is selected from a population of primary T lymphocytes and a tumor cell line of human T lymphocytes. Preferably, said tumor cell line of human T lymphocytes is the Karpas 299 cell line.

In a preferred embodiment, said inhibition test of the cytokine production is carried out by means of the MesoScale Discovery (MSD) assay.

The present invention will now be described for illustrative, but non-limiting, purposes, according to a preferred embodiment with particular reference to the attached figures, in which.

Figure 3:
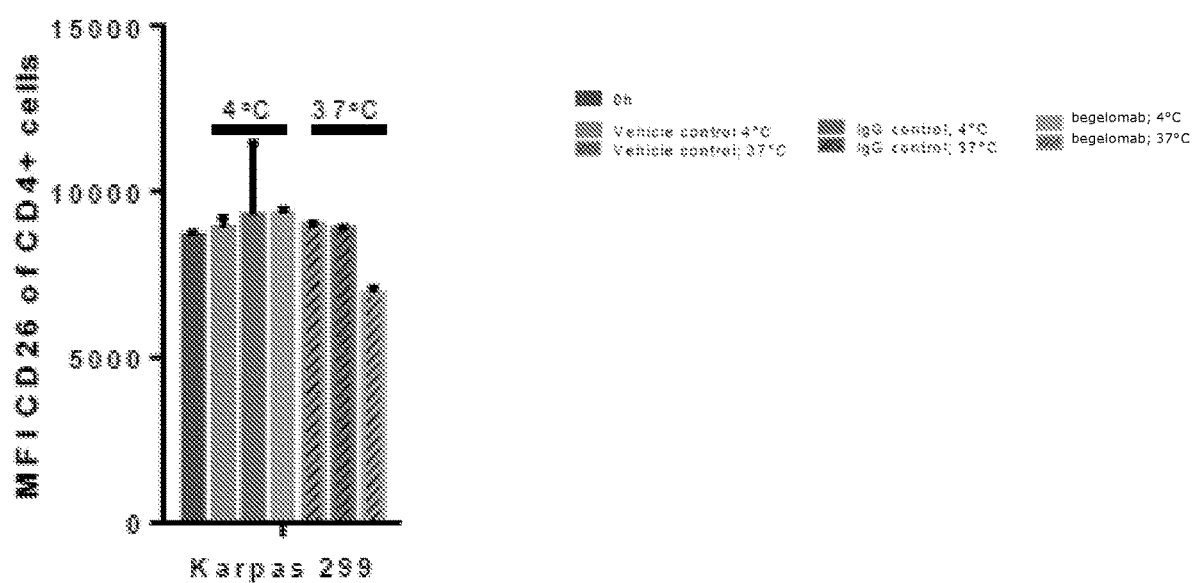
Figure 3:
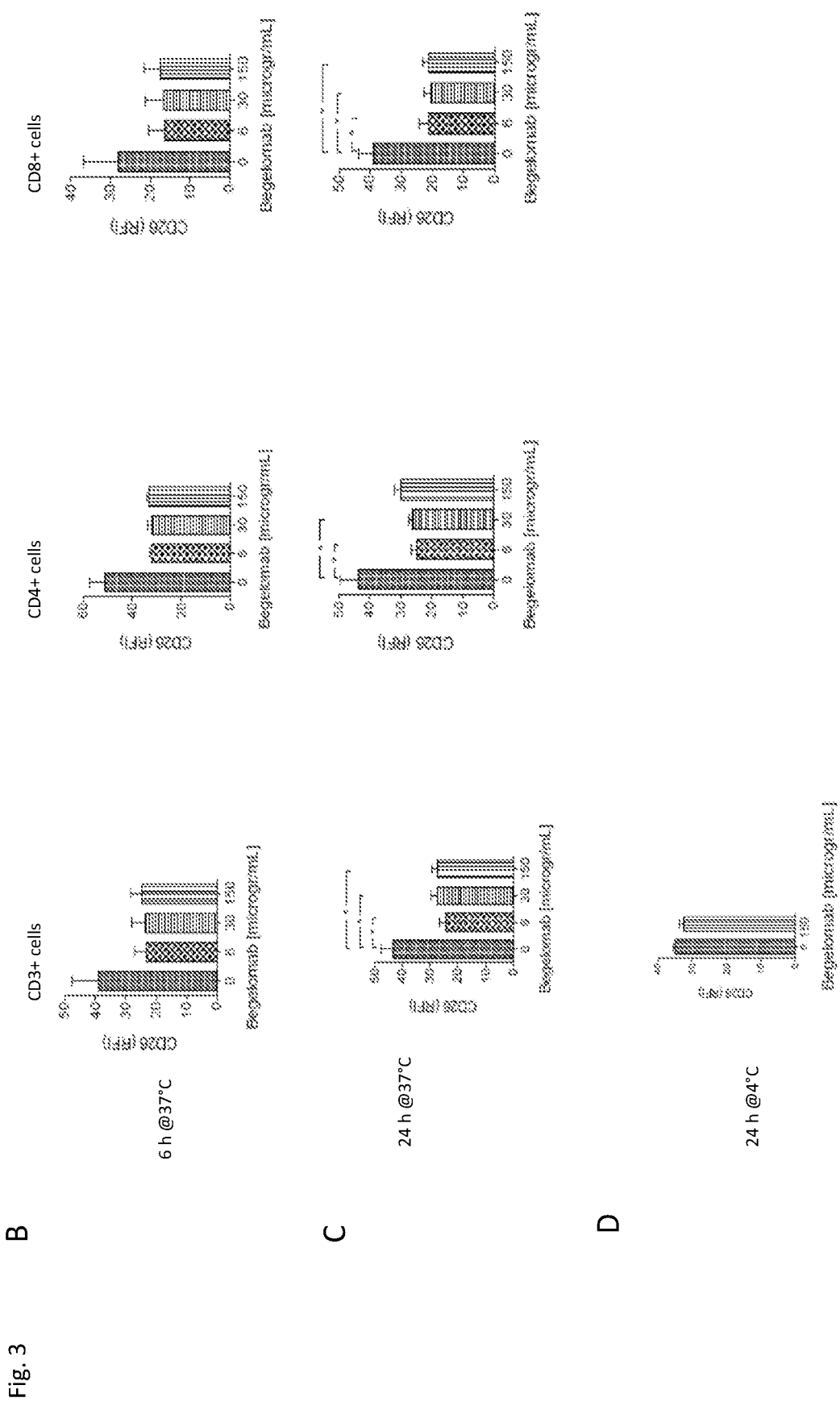

FIG. 3 shows the effect of Begelomab on the internalization of the CD26 receptor in Karpas 299 cells after 8 hrs incubation (panel A) and primary CD3+, CD4+, CD8+ T cells incubated at 4° C. and 37° C. (panels B, C, D) after 6 and 24 hrs.

Figure 4A:
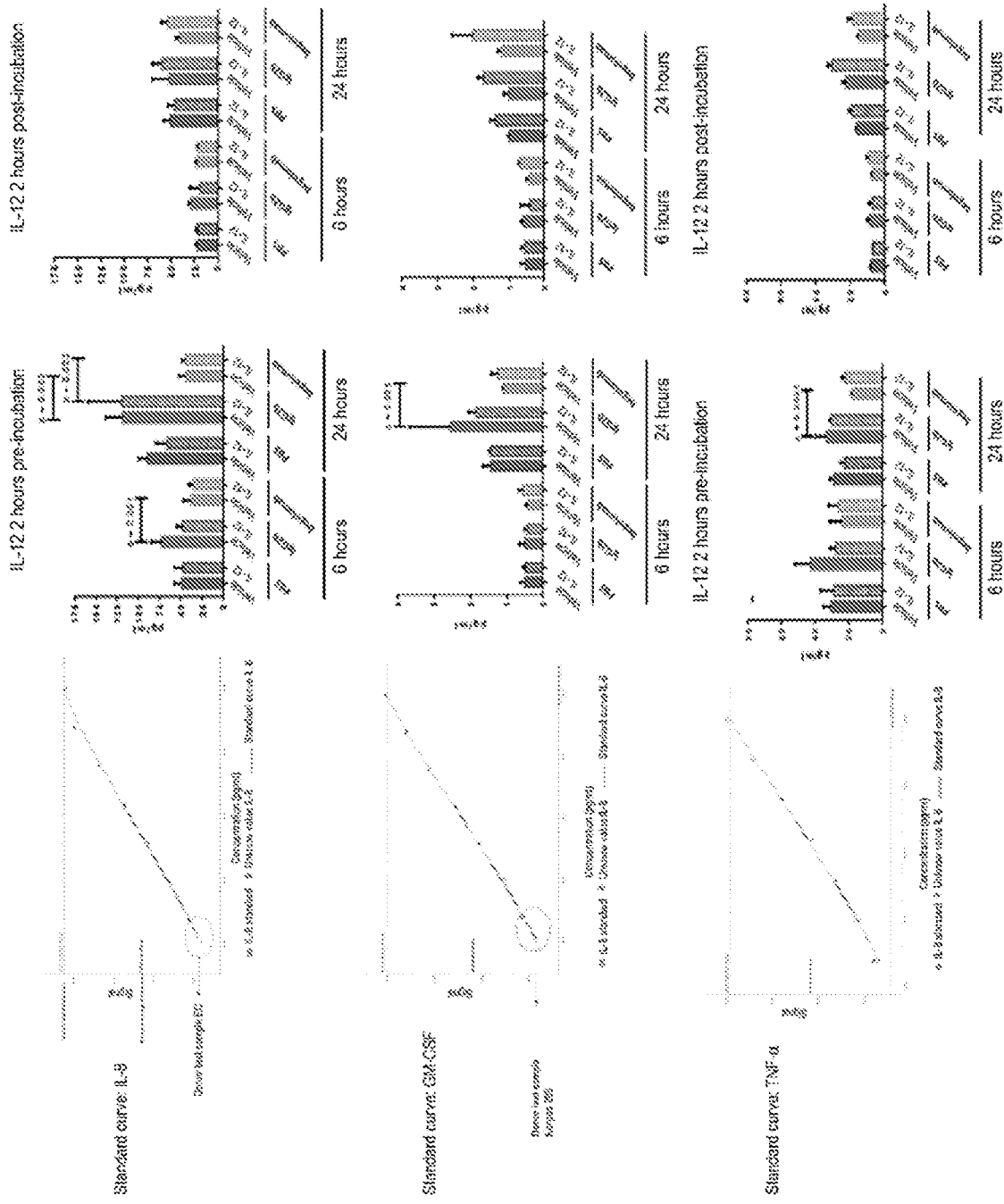
Figure 4B:
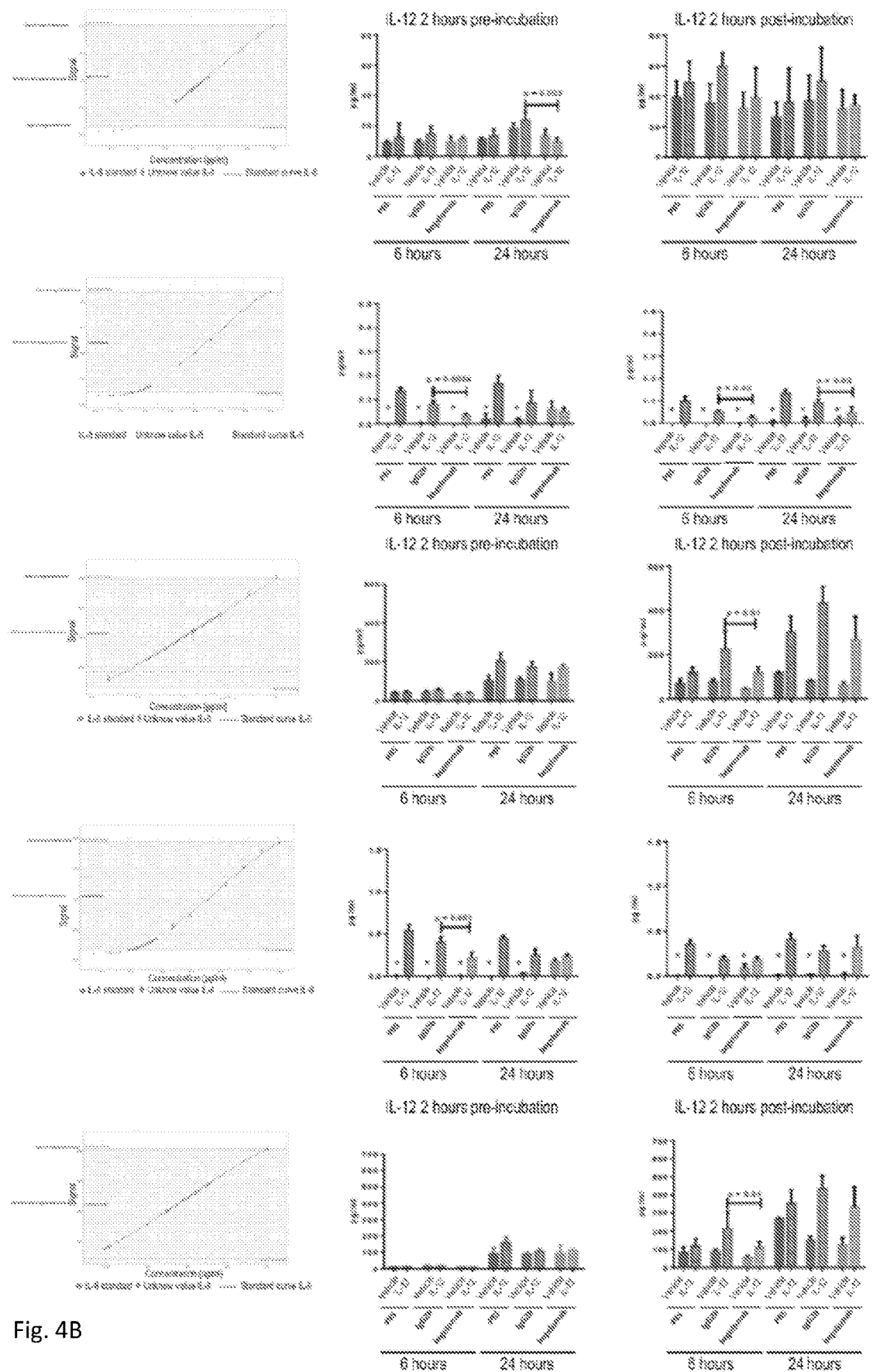

FIG. 4 shows the inhibition of the levels of cytokines IL-2, IL-8, IL-1β, GM-CSF, IL-6 and TNF-α induced by Begelomab in the T cell line Karpas 299 (panels A) and in primary T cells (panels B). In the graph, on the left on the ordinate axis, the electrochemiluminescence signal is indicated, whereas on the abscissas axis the corresponding concentration is indicated.

Figure 5:
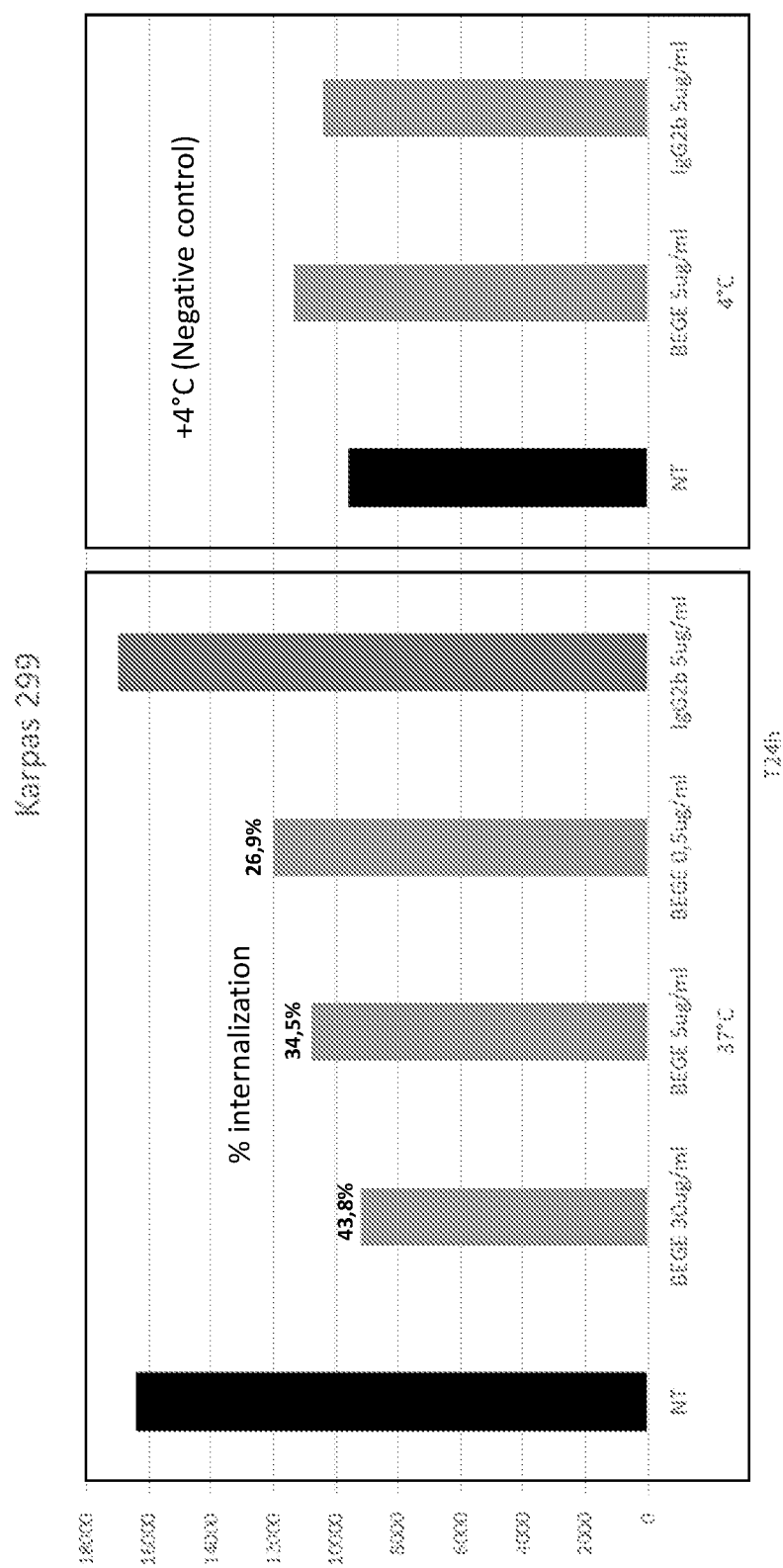

FIG. 5 shows the reduction in fluorescence associated with CD26 after 24 hours of treatment with begelomab in Karpas 299 cells.

Figure 6:
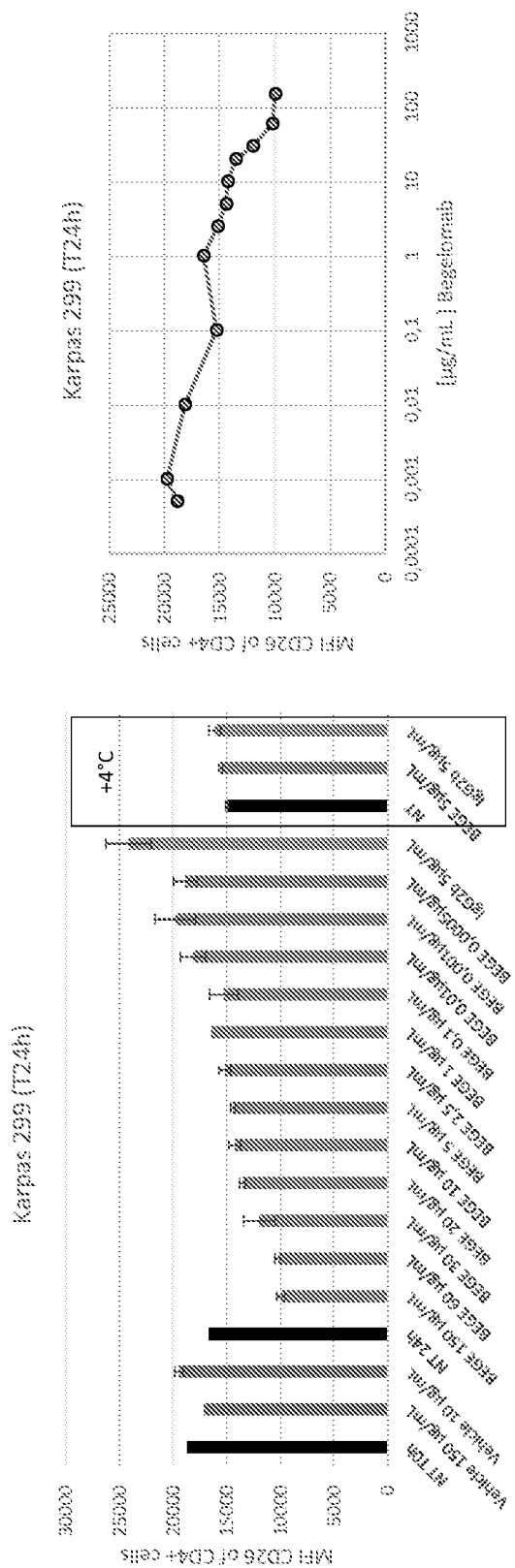

FIG. 6 shows the reduction in fluorescence associated with CD26 after 24 hours in Karpas 299 cells following treatment starting from a low dose of 0.0005 µg/mL ($3 \times 10^{-12}$ M) till the higher concentration of Begelomab equal to 150 µg/mL ($1 \times 10^{-6}$ M).

Figure 7:
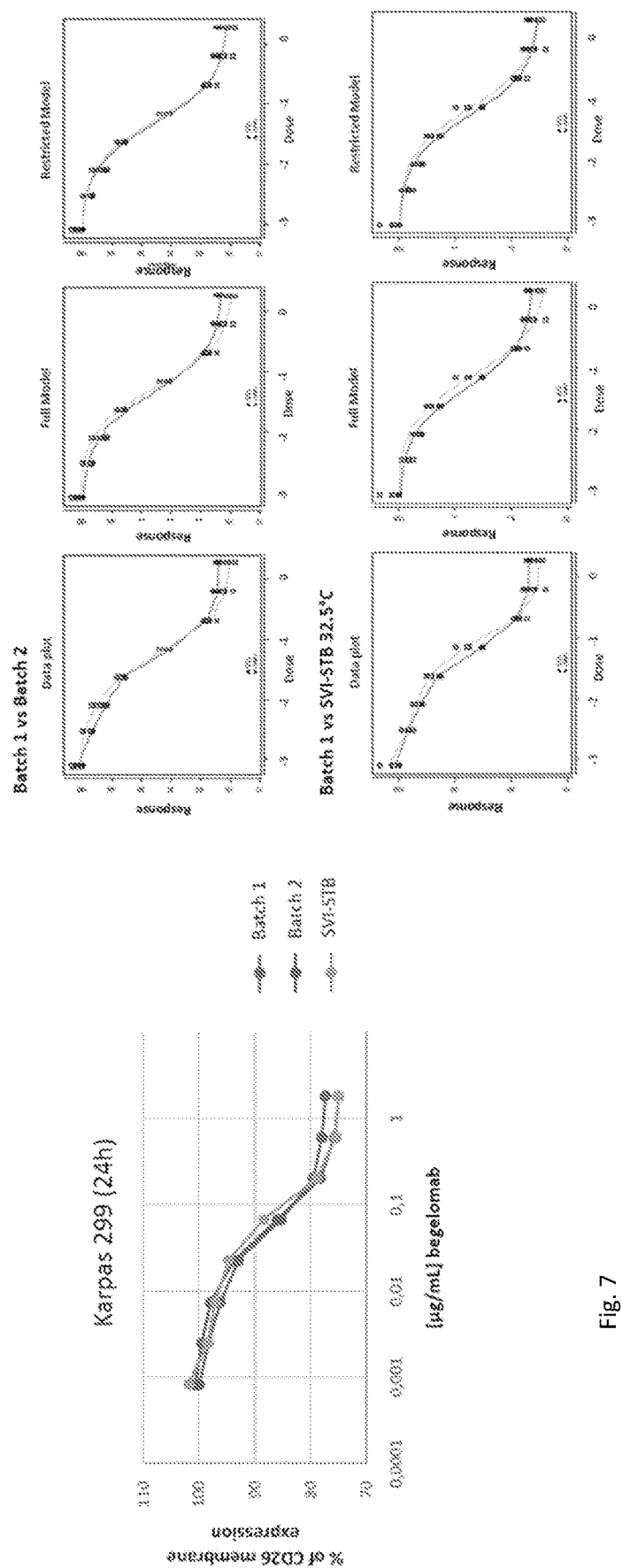

FIG. 7 shows the dose-response internalization curves of CD26 (RFI) acquired through FACS analysis performed on begelomab samples stored under different temperature conditions (SVI-STB is a sample with reduced potency, that is a sample put in accelerated stability at 32.5° C. for 6 months).

Figure 8:
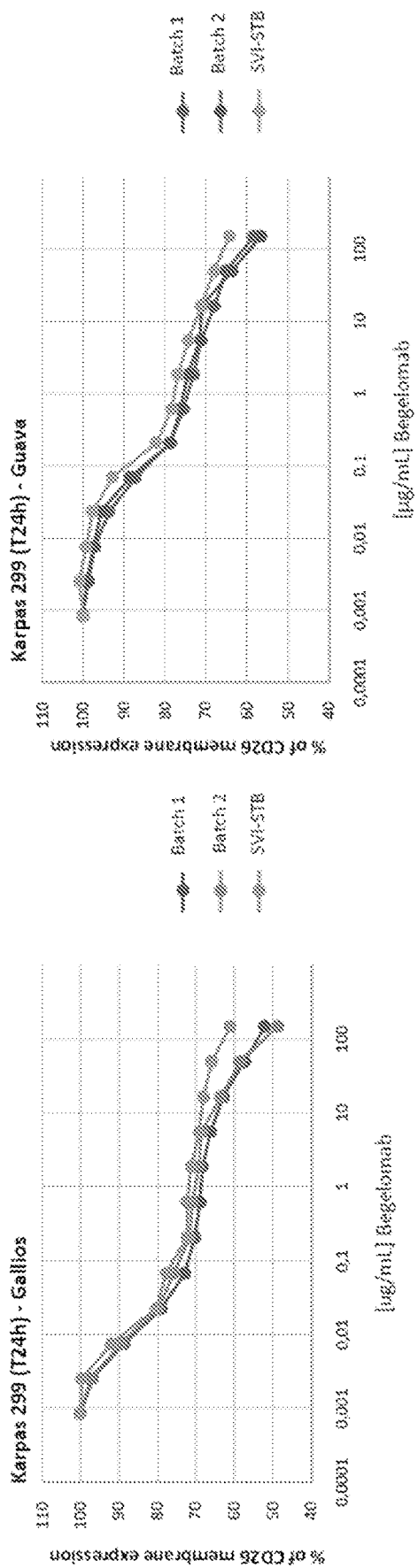

FIG. 8 shows the CD26 internalization curves (RFI) acquired through FACS analysis carried out on different cytofluorimeters.

Figure 9:
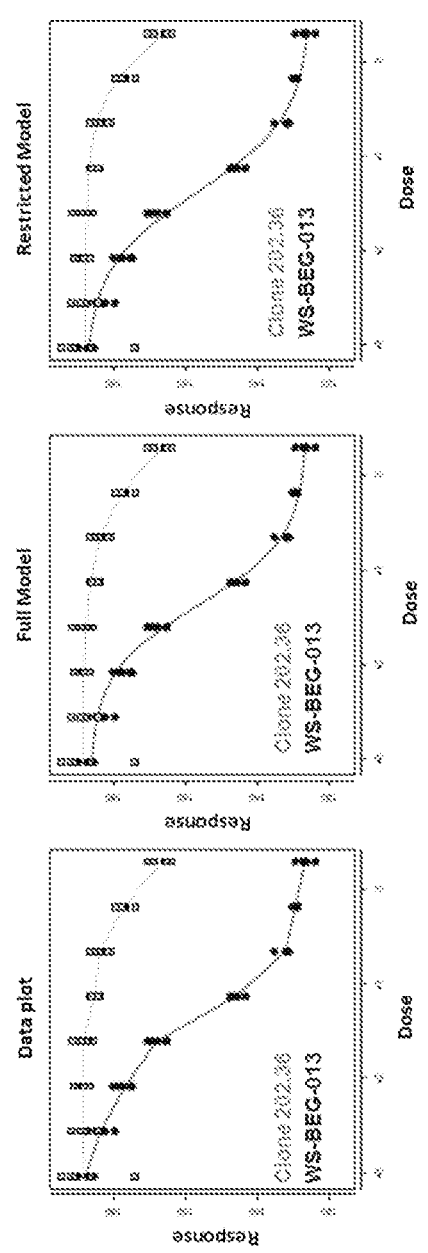

FIG. 9 shows the relative potency of the mouse monoclonal anti-hCD26 antibody (clone 202.36) observed with respect to begelomab (WS-BEG-013).

Figure 10:
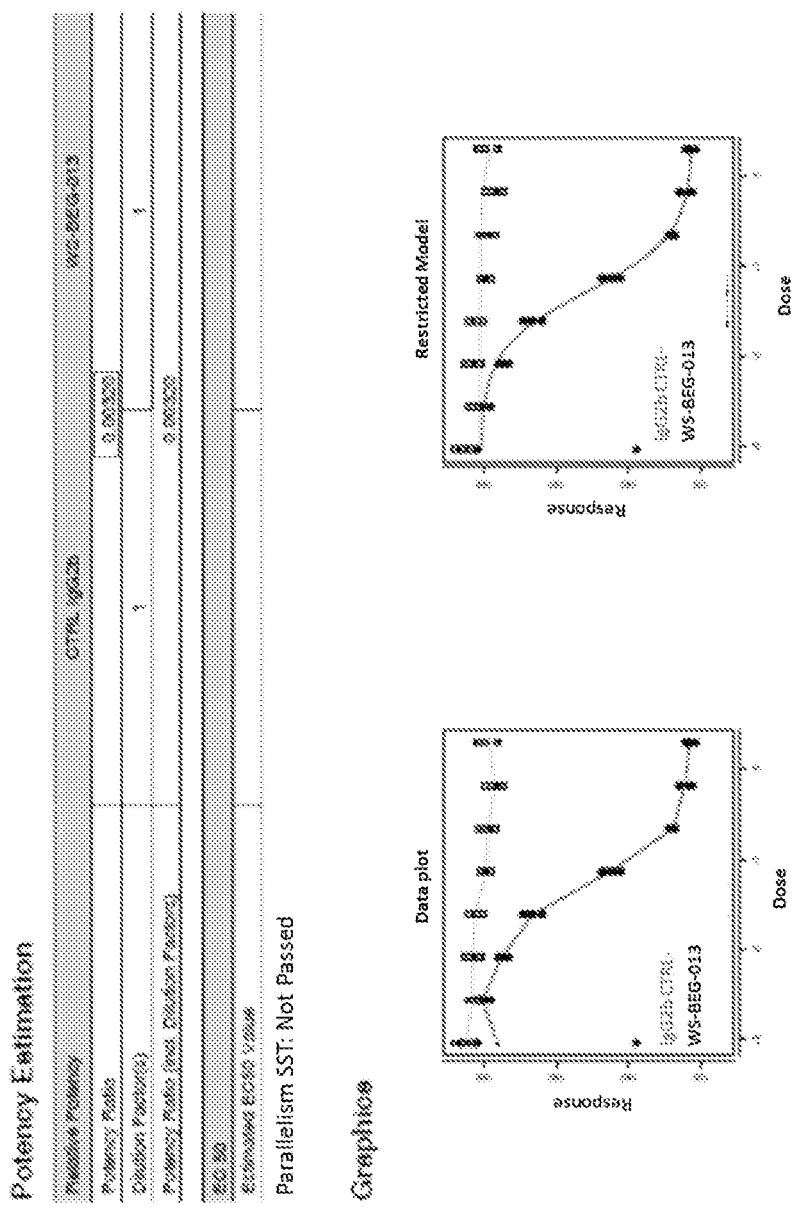

FIG. 10 shows the relative potency of the IgG2b mouse antibody, K isotype (Clone MG2b-57) observed with respect to begelomab (WS-BEG-013).

Figure 11:
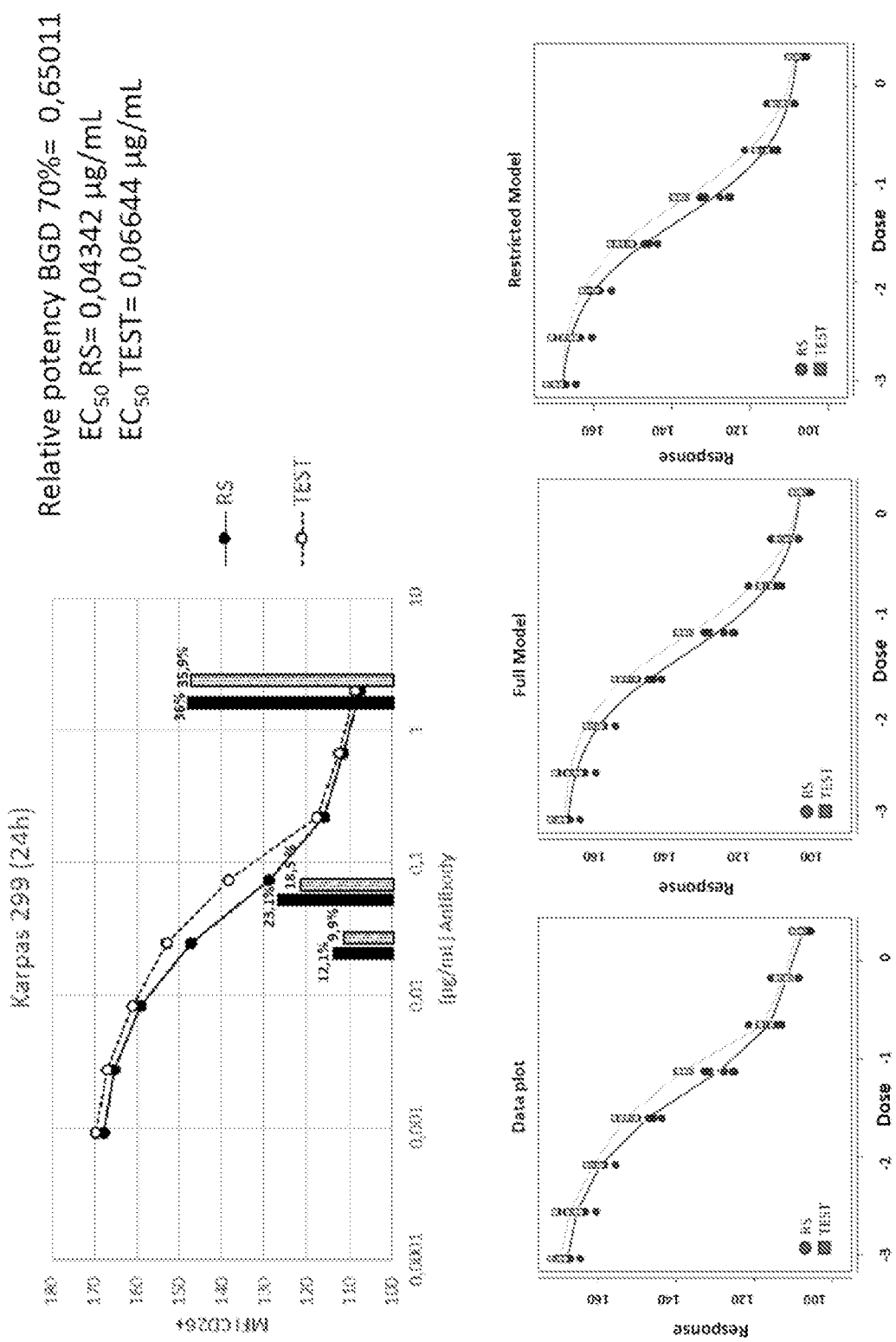

FIG. 11 shows the potency value of the tested sample (TEST) calculated with respect to the reference standard RS (begelomab), to demonstrate how the relative activity of any unknown sample named as TEST can be quantitatively measured with respect to the reference standard (RS).

Figure 12:
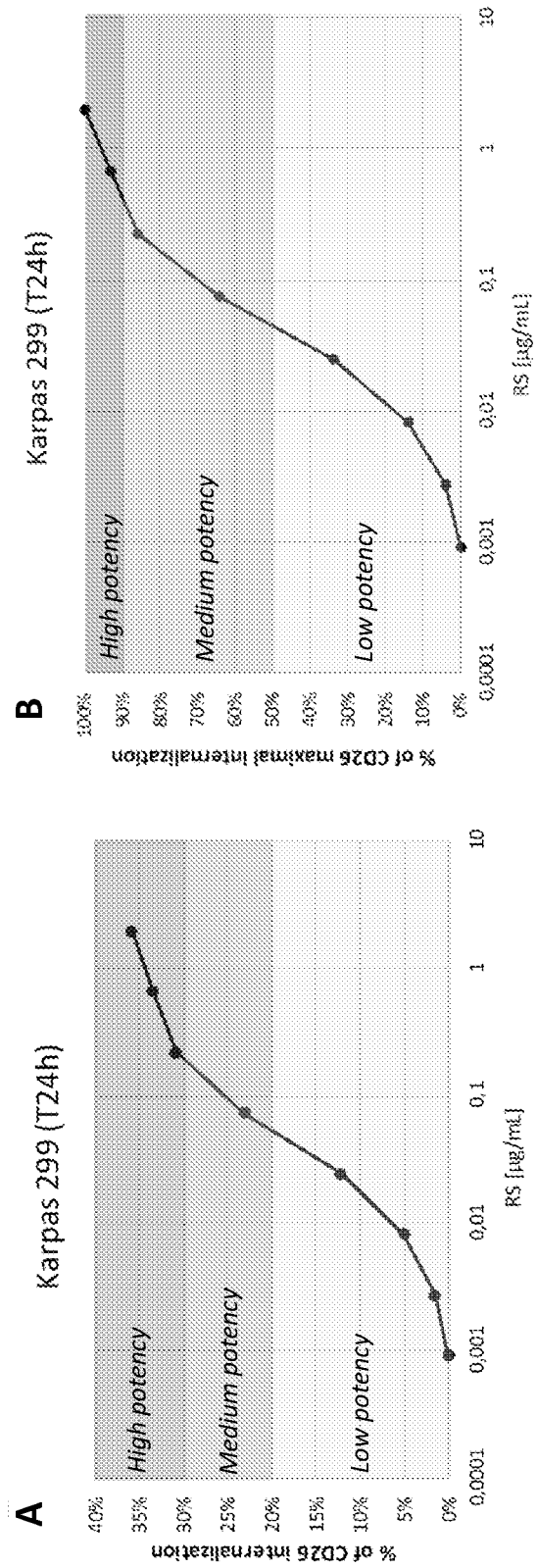

FIG. 12 shows two exemplary graphs of the criteria applied to determine low, medium or high potency.

In order to better illustrate the invention, the following examples are now provided which should be considered illustrative and non-limiting thereof.

EXAMPLE 1: STUDY ON THE MECHANISM OF ACTION OF THE MONOCLONAL ANTIBODY BEGELOMAB

The mechanism of action of Begelomab (anti-CD26) was studied in order to generate a test for evaluating the effectiveness of the antibody in vitro.

The development of this test, called potency test, is considerably important for measuring the biological activity of a given drug, as this activity is an essential component of the quality control of a molecule during the early development, advanced development and marketing phases within the scope of Quality Control as a batch release test.

Specifically, many biological products, such as monoclonal antibodies, exert their function through binding to a cellular or soluble target, subsequently triggering appropriate cellular events downstream of the molecular target.

The following were therefore evaluated:
The expression/overexpression of CD26 in human T cell lines and human primary T cells.
The internalization of CD26 following binding with begelomab.
The effect of Begelomab on the production and release of inflammatory cytokines.

Materials and Methods

Primary Cells and Cell Lines

The human T-cell line derives from T cells of Karpas 299 lymphoma that was purchased from SIGMA (Cat. 06072604-1VL). Karpas 299 cells were cultured in RPMI1640 with GlutaMAX (Gibco, cat. #72400), supplemented with 10% heat-inactivated bovine fetal serum (Sigma, cat. #F2442, the heat inactivation was effected in the laboratory), 1 IU/ml of penicillin/streptomycin (Gibco, cat. #15140), 2 mM of L-glutamine (Gibco, cat. #2503) and 50 µM of β-mercaptoethanol (Sigma-Aldrich, cat. #M3148). After thawing, the cells were expanded and cryopreserved.

The cell line was analyzed to evaluate the presence of mycoplasma (MycoAlert™, Lonza, cat. #LT-07) and was found negative to the latter. Peripheral blood mononuclear cells (PBMCs) were isolated through the Ficoll-Hypaque separation gradient (Lymphoprep, Fresenius) from buffy coats of three healthy donors obtained after informed consent according to a protocol approved by the San Raffaele Ethics Committee (IRB). In order to assess the cell viability, the PBMCs were stained with Trypan Blue and counted in Burker's chamber. The PBMCs were cultured in a complete medium (RPMI 10% FBS+1% PenStrep and Glutamine) with low doses of IL-2 (50 IU/mL) and IL-7 (5 µg/mL) at 37° C. throughout the night (o/n) before starting the experiment.

In order to determine the expression of CD26 on the cell surface of human primary CD4+ T cells and T cell lines, the antibody α-CD26-FITC clone BA5b was purchased (Biolegend, cat. #302704). The antibody was tested, in a dilution range, on the three donors of primary T cells and on Karpas 299 cells in order to determine the optimal concentration for cytofluorimetry. The optimal concentration will be used for determining the percentage of CD26 expression on human primary CD4+ T cells and
T cell lines, and for the internalization assay of CD26.

Expression of CD26 in T Cell Lines and Human Primary CD4+ T Cells

Primary CD4+ cells from two donors and Karpas 299 cells were plated in autoMACS buffer (Miltenyi, cat. #130-091-222) with the addition of 0.2% BSA (Miltenyi, cat. #130-091-376), at a density of 100,000 cells/well in 96-well V-bottom plates (Costar, cat. #3598). The cells were incubated for 15 minutes in a concentration range of α-CD26-FITC or α-IgG2α-FITC (Biolegend, cat. #400208) ranging from 2.5 µg/ml to 31.3 ng/ml. The cells were subsequently washed and fixed in 4% formaldehyde. The percentage of positive CD26 cells was determined by cytofluorimetry using FACSCanto II. IgG-FITC was used for determining non-specific bonds.

Quantification of the CD26 Expression on Human Primary Cells and T Cell Line

Cytofluorimetry was used for determining the amount of CD26 expressed on the cell membrane of primary peripheral blood mononuclear cells (PBMCs) and CD4+ T cells, and also on the Karpas 299 cell line. A CD4+ marking was added as T-cell marker. The primary CD4+ T cells from the three donors and Karpas 299 cells were plated in a MACS buffer with a density of 100,000 cells/well in 96-well V-bottomed plates. The cells were incubated with 10 µg/ml of α-CD26-FITC and 2.5 µg/ml of α-CD4 for 15 minutes. 10 µg/ml of α-IgG2α-FITC and 2.5 µg/ml of α-IgG2b-APC (Biolegend, cat. 400612) were added to allow gating. The cells were subsequently washed and fixed in 4% formaldehyde. The percentage of CD4+ and CD26+ cells was determined by cytofluorimetry using FACSCanto II.

Internalization Assay of CD26

The capacity of Begelomab of inducing the internalization of the CD26 receptor in T cells (both in human primary T cells and in the T-cell line) was determined by cytofluorimetric analysis. The assay was carried out in two independent experiments. CD4+ T cells were isolated from three 3 buffy coats per experiment. Subsequently, both PBMCs and the isolated cells were marked with an anti-CD4 and anti-CD26 antibody to determine the purity of the isolated cell population, as well as the percentage of CD26 cells before the experiment. In addition, a viability dye was added to ensure that the experiment was carried out on live cells. The cells were analyzed by cytofluorimetry.

The CD4+ cells were assessed as being of good quality as the purity of the CD4+ population was found to be >95%; the percentage of CD26+ cells in the CD4+ population was >75%. The T-cell line was plated for the whole night (o/n) with 100,000 cells/well in 96-well flat-bottom plates (Corning Costar, cat. #3598) coated with 2 µg/ml of anti-CD3/anti-CD28 (eBioscience, cat. #16-0037-85 and 16-0289-85, respectively), and incubating them for 2 hours at 37° C. After an o/n incubation, the medium was changed and the cells incubated with 0.03 mg/ml ($2\times10^{-7}$M) of begelomab, IgG2b as control (Sigma-Aldrich, cat. #SAB4700729 or Biolegend, cat. #401202) or PBS (Gibco, cat. #10010) as a control vehicle in a total volume of 100 µl. Each condition was tested in triplicate (three cell wells/condition). The treatment was carried out at 4° C. and at 37° C., for 8 hours. The cells were subsequently marked and the percentage of CD26+ cells in CD4+ cells was determined by cytofluorimetry. In addition, a group of cells were marked and analyzed before the start of the treatment to determine the percentage of CD4+CD26+ cells at time zero. On the day of the experiment, the PBMCs were isolated by centrifugation at 1,500 rpm for 5 minutes and incubated with begelomab at different concentrations for 6 and 24 hours, respectively. After incubation with begelomab, the PBMCs were washed and marked with the following monoclonal antibodies: human antibodies against CD3, CD4, CD8 and CD26 conjugated with FITC-, PE-, APC, APC-H7-(Biolegend). It has previously been shown that the monoclonal antibody against CD26 can bind a different epitope from that of Begelomab. The antibody conjugated with the fluorophore against the isotype corresponding to that of Begelomab (IgG2b) was always used as a negative control. The samples were analyzed using the FACS Canto II flow cytometer (BD Biosciences). All data were analyzed with Flow Jo software (Tree Star Inc.) and expressed as relative fluorescence intensity (RFI) of CD4+ or CD8+ cells. This value is calculated by dividing the average fluorescence intensity of the sample marked with anti-CD26 with the corresponding isotype control.

9-Plex MSD Assay for Pro-Inflammatory Cytokines

In order to evaluate the effect of begelomab in the activation of T cells, the production of pro-inflammatory cytokines was evaluated.

For this purpose, the MesoScale Discovery (MSD) assay was used, i.e. a 9-plex assay for human pro-inflammatory cytokines (cat. #15007B-2). Both the primary T cells and the Karpas 299 T-cell line were plated with 100,000 cells/well in 96-well flat-bottom plates coated with anti-CD3/anti-CD28, as described above (section 4.1.1.2), and incubated o/n.

Figure 1:
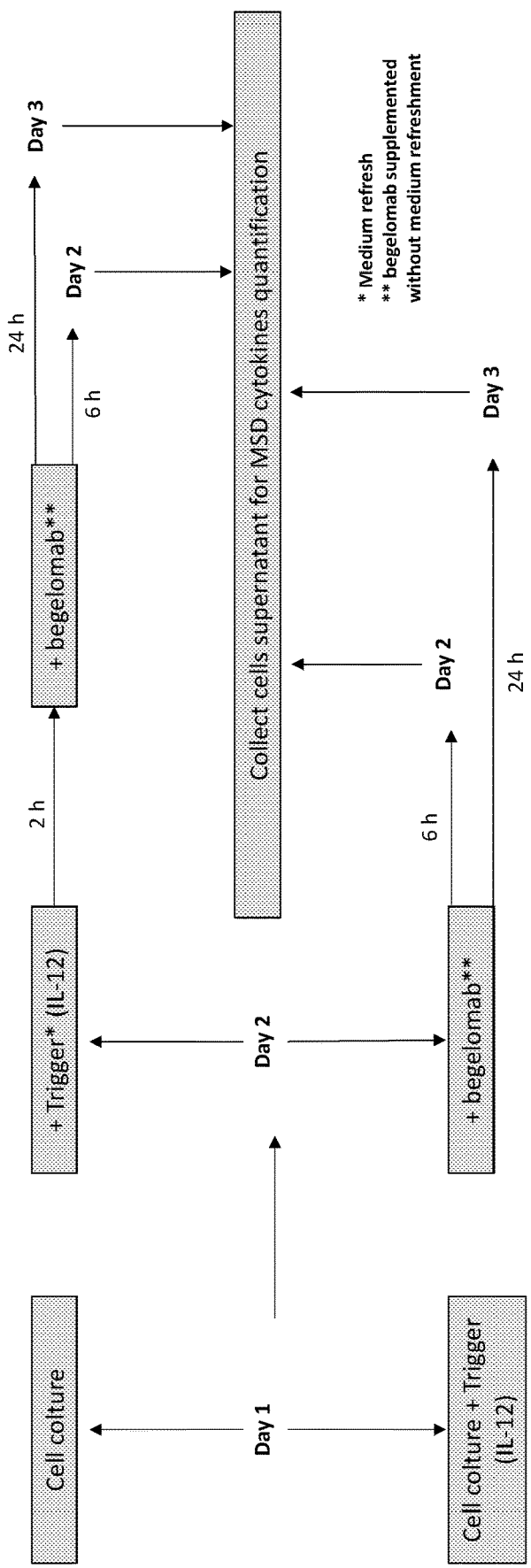
FIG. 1 shows the experimental scheme of the cell culture for the analysis of proinflammatory cytokine levels with the MSD assay.

The cells were kept in a RPMI 1640 medium with GlutaMAX and supplemented with 10% HI-FBS, 1% penicillin/streptomycin, 2 mM of L-glutamine and 50 µM of β-mercaptoethanol. The cells were treated with IL-12 and Begelomab as described in FIG. 1. In short, the cells were either pre-incubated o/n with 20 ng/ml di IL-12 (R&D systems, cat. #219-IL-0059) and control vehicle (0.1% bovine serum albumin (BSA, Sigma-Aldrich, cat. #A2153-1 kg)-PBS) or incubated o/n without IL-12/control vehicle. The following day, the cells without o/n pre-incubation of IL-12 were incubated for 2 hours with 20 ng/ml of IL-12. Subsequently all the cells were incubated with 0.03 mg/ml ($2 \times 10^{-7}$ M) of IgG2b (Biolegend), Begelomab or PBS control vehicle for 6 hours or 24 hours. In all the experiments, the supernatant was collected after the expected period of time and frozen at $-80°$ C. until new analyses.

In order to test the effect of the "coating" with anti-CD3 and anti-CD28 on cytokine secretion, the cells were tested on coated and uncoated plates and pre-incubated o/n with IL-12 and subsequently treated for 24 hours with Begelomab/IgG2b/PBS. Cytokine MSD analysis detects levels of interleukin 2 (IL-2), IL-8, IL-1β, the granulocyte-macrophage colony-stimulating factor (GM-CSF), interferon-gamma (IFN-γ), IL-6, IL-10, tumor necrosis factor-alpha (TNF-α) and IL-12p'70. The MSD cytokine assay was conducted according to the manufacturer's instructions, the plates were in fact blocked o/n at 4° C. instead of 1 hour at room temperature, to prevent potential non-specific bonds. The standardization curve was prepared using the medium adopted during the cellular phase of the experiment. MSD Discovery Workbench 4.0.12 software was used for generating the standardization curves and for calculating the cytokine concentration (pg/ml). The values of the samples were entered into the standardization curve to determine whether they were within its range. The graphs for all the cytokines were prepared with GraphPad Prism 6. Initially, an inhibition by Begelomab twice higher than the IgG2b control for effecting the statistical analysis, was arbitrarily set as a threshold level.

However, as various conditions showed a 1.9-fold inhibition, this threshold value was shifted to 1.9. In order to evaluate the statistically significant differences, within a treatment condition, the two-way ANOVA test was used with a post-hoc Turkey test in Graph Pad Prism 6.0, obtaining a p value adjusted on multiple tests.

Results

Figure 2:
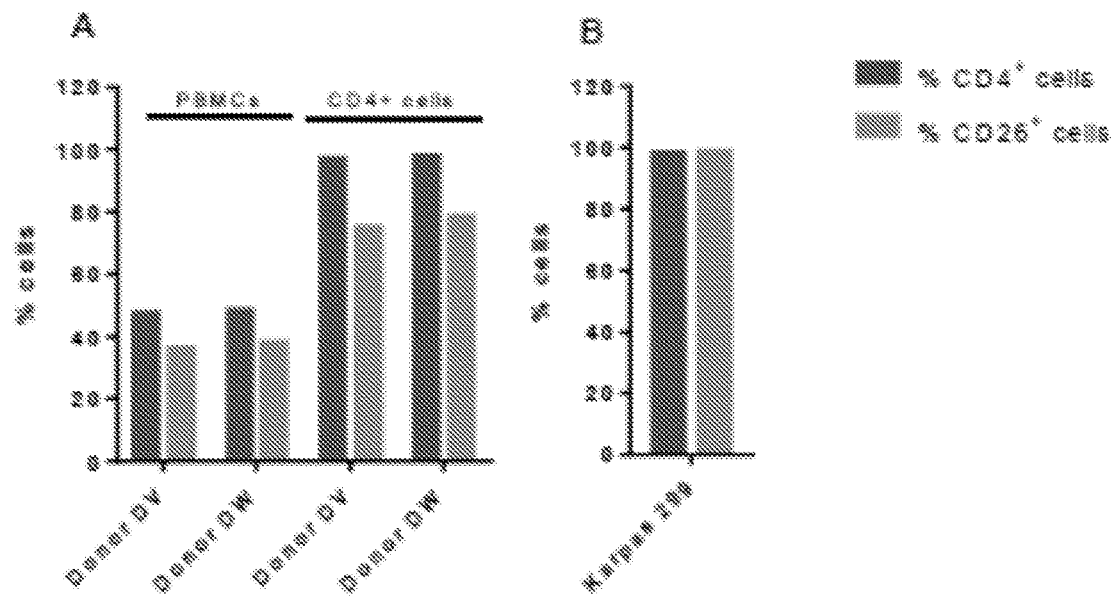
FIG. 2 shows the cytofluorimetric analysis of the percentage of CD4+ cells (dark column) and CD26+ cells (light column) in primary mononuclear cells of the peripheral blood and purified CD4+ T cells (A) and human T cell line Karpas 299 (B).

Expression/Overexpression of CD26 in Human T Cell Lines and in Human Primary T Cells FIG. 2 shows the percentage of CD4+ and CD26+ cells within the population of mononuclear primary cells deriving from peripheral blood, in purified CD4+ T cells and in the Karpas 299 line. The results obtained by cytofluorimetry show that the percentage of CD4+ and CD26+ cells in the primary mononuclear cells is approximately >45% and >35% respectively, after isolation of the CD4+ T cells, these percentages become >95% and >75% respectively (FIG. 2, panel A). Almost all of the Karpas 299 cells express CD4 (>95%) as well as high levels of CD26 (>95%) (FIG. 2, panel B). In conclusion, the percentage of CD26 positive cells within the isolated primary CD4+ T population and in the Karpas 299 cell line is approximately 75% and 95% respectively. The above percentage is also sufficient for measuring changes in the CD26 levels in the subsequent experimental steps.

Internalization of CD26

Cytofluorimetric analysis was used for determining the internalization of begelomab-induced CD26 in primary T cells and in T cell lines. The same analysis was also used for identifying the dose-dependent relationship between the decrease in the CD26 presence and the concentrations of begelomab. In the Karpas 299 T cell line, the percentage of CD26+ cells was determined as well as the average fluorescence intensity (MFI) of CD26+ in the CD4+ population. In the T Karpas 299 cell line, a reduction of CD26 MFI in the CD4+ population was observed, only at 37° C., after 8 hours (an inhibition of 7% after 4 hrs—data not reported in the figure—and 22.3% after 8 hrs, respectively) (FIG. 3, panel A). This reduction is statistically significant in the MFI of CD26 in the CD4+ population measured after 8 hours of incubation with begelomab at 37° C. with respect to the incubation effected at 4° C., i.e. when all biological processes are inhibited by the low temperature. The data obtained indicate that the number of CD26 receptors per single cell decreases in the Karpas 299 cells at 37° C. following the binding with begelomab. As the same biological phenomenon was not observed at 4° C., it can be concluded that the internalization of the CD26 receptor following binding with begelomab represents the mechanism of action of the antibody in the Karpas 299 T cell line. To ensure that the internalization of the CD26 receptor in Karpas 299 cells induced by the binding with begelomab could be used as a potency test for batch release for clinical development, a dose-response experiment was carried out. In the above-mentioned experiment, Karpas 299 cells were treated with increasing concentrations of begelomab at 37 degrees and specifically 0.5 µg/ml ($3 \times 10^{-9}$ M), 5 µg/ml ($3 \times 10^{-8}$ M) and 30 µg/ml ($2 \times 10^{-7}$ M) for 24 hours (FIG. 5). The results obtained are of great interest as it has been found that increasing concentrations of anti-CD26 are capable of inducing a progressive increase in the internalization of CD26 expressed in the membrane. In particular, doses of 0.5 µg/ml, 5 µg/ml and 30 µg/ml of begelomab, $3 \times 10^{-9}$ M, $3 \times 10^{-8}$ M and $2 \times 10^{-7}$ M respectively, correspond to internalization percentages of 26.9%, 34.5% and 43.8%. This dose-response effect is a necessary condition for the development of a potency test.

In order to evaluate the effect of begelomab on primary T cells, the mononuclear cells deriving from peripheral blood were incubated with begelomab under three different conditions (6 µg/ml; 30 µg/ml and 150 µg/ml, $4 \times 10^{-8}$ M, $2 \times 10^{-7}$ M and $1 \times 10^{-6}$ M respectively) for 6 and 24 hours at 37° C. Following incubation, the cells were immediately marked to evaluate their CD26 expression. As control, the mononuclear cells were incubated with the highest concentration of begelomab (150 µg/ml, i.e. $1 \times 10^{-6}$ M) at 4° C. After 6 hours, an appreciable, although not significant, reduction in the internalization levels of CD26 (RFI) was observed compared to baseline levels of CD26 in CD3+, CD4+ and CD8+ T cells (FIG. 3, panel B). Statistically significant results (*, P<0.05) were obtained however at 24 hours, in particular for CD8+ T cells (FIG. 3, panel C). As previously observed for the Karpas 299 cell line, the effect of CD26 down-regulation decreases when the mononuclear cells are incubated with begelomab at 4° C. (FIG. 3, panel D), suggesting an active blocking phenomenon of the internalization of the antibody-CD26 complex. In short, after 24 hours incubation with begelomab, the expression of CD26 is reduced to 43.8% in Karpas 299 cells when treated with concentrations of 30 μg/ml ($2 \times 10^{-7}$ M) of begelomab and this phenomenon is dependent on the dose of anti-CD26 (FIG. 5). As expected, at 4° C. no changes in the CD26 expression were observed on the surface of the cells analyzed. The results obtained clearly indicate that the CD26 receptor is internalized in response to the binding with begelomab with the consequent elimination of a crucial activation signal for the subpopulation of CD26+ T cells.

Release of Pro-Inflammatory Cytokines

Considering that the internalization of CD26 could have various downstream effects on the T cell activation, the levels of some pro-inflammatory cytokines were evaluated following treatment with begelomab in primary T cells and Karpas 299 cells.

Inflammatory cytokines can be classified in two groups: group 1) involved in acute inflammation; group 2) responsible for chronic inflammation. Cytokines such as IL-1, TNF-α, IL-6, IL-11, IL-8 and other chemokines, G-CSF and GM-CSF, belong to the first group. The second group can be further divided into cytokines that mediate the humoral response such as IL-4, IL-5, IL-6, IL-7 and IL-13 and those that mediate the cellular response such as IL-1, IL-2, IL-3, IL-4, IL-7, IL-9, IL-10, IL-12, interferons, transforming growth factor-β and tumor necrosis factor α and β (Shaikh P Z, 2011).

Pro-inflammatory cytokines are molecules involved in a series of autoimmune diseases such as rheumatoid arthritis, multiple sclerosis, GvHD. In the pathogenesis of these diseases, CD26 plays a key role specifically in the inflammation process. For this reason, the inhibition of some pro-inflammatory cytokines by begelomab was evaluated. More specifically, the levels of the following cytokines were analyzed: Interleukin-2 (IL-2), IL-8, IL-1β, the granulocyte-macrophage colony-stimulating factor (GM-CSF), interferon-gamma (IFN-γ), IL-6, IL-10, the tumor necrosis factor-alpha (TNF-α) and IL-12p70. A series of dilutions of the supernatant samples was effected as a pre-test in the assay and the results indicated that the undiluted samples were in the standardization curve range for all cytokines, except in the supernatants of IL-12p70 cells exposed to IL-12 as a signal (not shown). For this reason, 25 μl of an undiluted standard supernatant was tested in the MSD assay. In both experiments, the standard curves of all the cytokines in all the assay plates showed well-calibrated curves.

The samples to be analyzed were inserted in the standard charts to determine whether they were within detection range. The levels of all cytokines, except for IL-12p′70, were measured and analyzed, although changes in the cytokine levels were observed between primary T cell donors and the Karpas 299 T cell line, with levels below the detection limit under certain conditions. IL-1β and IL-6 levels were very low in all cell populations analyzed in both experiments. Treatment of the cells with IL-12 clearly induces the production of IL-1β, IFN-γ, IL-6 and IL-10 in multiple conditions, as previously reported in literature (Vacaflores A. et al., 2016). The inhibition of the production of cytokines following treatment with Begelomab was therefore observed for IL-2, IL-8, IL-1β, the granulocytic-macrophage colony-stimulating factor (GM-CSF), IL-6 and the tumor necrosis factor alpha (TNF-α) (FIG. 4).

A strong decrease in IL-8 and IL-1β levels, following incubation with begelomab, was observed under the same conditions both in the Karpas 299 cells and in the primary T cells.

The following Table 2 provides an overview of the inhibitory effect of begelomab in the secretion of different cytokines in primary T cells and Karpas 299 cells, showing in particular inhibition of the pro-inflammatory cytokine levels induced by begelomab after incubation of the cells at 37° C. for 6 or 24 hours.

TABLE 2

| Cell type | Cytokines | | | | | |
|---|---|---|---|---|---|---|
| | IL-2 | IL-6 | IL-8 | GM-CSF | IL-1β | TNFα |
| Primary T cells | + | + | — | + | + | + |
| Karpas 299 cell line | — | — | + | + | — | + |

—: No inhibition
+: With inhibition

Furthermore, in order to test the effect of "coating" on cytokine secretion, the cells were tested on coated and uncoated plates with anti-CD3/anti-CD28 and treated with IL-12, Begelomab or the appropriate control vehicle, as described in the section "Materials & Methods". In general, it was observed that the cytokine levels were not detectable or proved to be lower in uncoated plates with respect to coated plates. This indicates that coating is essential for creating an assay window for studying the effect of Begelomab in assessing cytokine levels. The effect of Begelomab on the measurement of cytokine levels using uncoated plates was consequently not further analyzed. On the basis of this experiment, the results obtained showed that begelomab is able to strongly reduce the production of specific cytokines such as IL-8, IL-1β and IL-6 both in primary T cells and in Karpas 299 cells, highlighting the mechanism of action of anti-CD26 (Begelomab) in the treatment of autoimmune diseases.

EXAMPLE 2: CELLULAR ASSAY SETUP FOR DETERMINING THE POTENCY OF ANTI-CD26 LIGANDS

The aim of the present experimental part is to set up a cellular assay for the activity of anti-CD26 ligands, starting from the known anti-CD26 monoclonal antibody, begelomab.

Begelomab is an anti-CD26 monoclonal antibody produced by hybridoma cells whose clinical target is the inhibition of the activation of T lymphocytes of the donor in allogeneic transplants.

The objective of the assay is to measure the variation in the CD26 levels present on the cell membrane of human T-lymphocytes (Karpas 299, CD4 positive) following treatment of the latter in vitro with increasing concentrations of begelomab.

CD26 is a membrane glycoprotein involved in the activation of T-lymphocytes with a dipeptidyl-peptidase activity. Preliminary data demonstrate the capacity of begelomab of inducing an internalization of CD26 on the surface of human T-lymphocytes and Karpas 299 cells following a 24-hour treatment.

Specifically, the cells are incubated at 37° C. for 24 hours with increasing concentrations of begelomab and subsequently stained with two antibodies, capable of respectively binding the CD4 and CD26 receptor, and conjugated with fluorophores which emit at different wavelengths. During the FACS analysis, for each concentration of begelomab tested, the fluorescence intensity is measured proportional to the amount of CD26 present on the cell surface of each single cell. This parameter is then quantified by the instrument by calculating the median of 20,000 single fluorescence signal-acquisition events, selected on the positive CD4 cell population.

Staining Protocol of Cell Samples and FACS Analysis

At the expiration of the pre-established incubation time with begelomab, the cell samples are processed according to the following staining protocol with antibodies conjugated with fluorophores and then analyzed by FACS for surface CD26 expression:

Transferring the contents of each well to 1.5 mL Eppendorf;
Centrifuging at 10,000 rpm for 5 minutes;
Washing the pellet with 1 mL of cold DPBS;
Centrifuging at 10,000 rpm for 5 minutes;
Drying the pellet and staining with the following antibodies according to the incubation protocol for FACS analysis as described below in Table 3.

CD26 to be calculated as the average value of all the events recorded during the acquisition (selected within the CD4 positive cell population).

Results

The biological activity of begelomab was measured as the capacity of inducing the internalization of CD26 present on the surface of the cell membrane of Karpas 299 cells.

The quantity of CD26 internalized following treatment with increasing concentrations of begelomab was measured as a decrease in the average value for fluorescence emitted by the specific antibody (APC Mouse Anti-Human CD26, Clone M-A261 RUO BD Pharmigen code 563670) bound to the CD26 expressed on the surface of the cell membrane.

The aim is to generate concentration-response curves for each batch of product to be compared with the concentration-response curve obtained by treating the cells with the Working Standard (WS) by means of a comparative potency test of the lot vs. WS, in which the parallelism of the curves is a prerequisite of the suitability of the assay (Parallelism Test performed with PLA.3 Analysis Software).

As can be seen from the graph in FIG. 5, after 24 hours of treatment with begelomab, there is a reduction in fluorescence associated with CD26 of about 40% for Karpas 299 cells.

Furthermore, this effect in Karpas 299 cells proves to be concentration-response, a condition considered essential for the development of a cellular assay.

The effect observed is specific for begelomab as the IgG2b pool (IgG class to which begelomab belongs) does not induce CD26 internalization under any of the conditions tested.

TABLE 3

| Antibody | Fluorophore | Target | µl/tube | DPBS-5% FBS/tube | Cells/tube | Incubation time |
| --- | --- | --- | --- | --- | --- | --- |
| FITC Mouse Anti-Human CD4, Clone RPA-T4 (BD Pharmigen cat. 555346) | FITC | CD4 | 20 µ | 100 µl | 1.00E+06 | 30 mm. |
| APC Mouse Anti-Human CD26, Clone M-A261 (RUO) (BD Pharmigen cat. 563670) | APC | CD26 | 5 µ | 100 µl | 1.00E+06 | 30 mm. |

Vortexing the sample and incubating at R.T. for 30 minutes in the dark;
Adding 1 mL of DPBS and centrifuging at 10,000 rpm for 5 minutes;
Discharging the supernatant and washing the pellet with 1 mL of cold DPBS 1×;
Centrifuging at 10,000 rpm for 5 minutes;
Resuspending the cell pellet at a concentration of 0.7-1E6 cells/mL in DPBS-5% FBS and storing the samples in the dark at +4° C. until the FACS reading. If the reading cannot be effected during the day the cells are fixed with the addition of paraformaldehyde at the final concentration of 0.36%.

During the FACS analysis, for each concentration of begelomab tested, the fluorescence intensity is measured relating to the amount of CD26 present on the cell surface of each single CD4 positive cell. This parameter is then quantified by the instrument as an average value deriving from the acquisition of the fluorescence of 20,000 events, selected within the CD4 positive cell population. For the acquisition of the two fluorescences associated with FITC and APC, it is not necessary to carry out the compensation activity as two fluorophores emit at different wavelengths.

The data are subsequently reprocessed using the BD FACS Diva program which allows the expression level of In order to achieve optimal growth conditions for evaluating the biological effect, it was decided to proceed by repeating the incubation with begelomab for 24 hours and to use CD3+ T lymphocytes after stimulation with Dynabeads Human T-Activator CD3/CD28 (Gibco kit, Life Technologies, code 11131D).

% Internalization of CD26

As can be seen from the graph in FIG. 6, after 24 hours of treatment with begelomab there is a reduction in fluorescence associated with CD26 of about 48% for Karpas 299 cells following treatment with the highest concentration of Begelomab (equal to 150 µg/mL, or $1\times10^{-6}$ M).

The expansion of the concentration-response curve allowed the lower response limit to be reached, which is equal to 0.01 µg/mL ($7\times10^{-11}$ M).

The lack of effect of the IgG2b pool (used as negative control) was confirmed.

The subsequent assays were designed to reduce the complexity of the curve (to verify whether the curve has a monophasic or multi-phase pattern).

Potency Evaluation in Different Samples of Begelomab

A potency evaluation of three begelomab samples was then carried out, one of which was stored under conditions of accelerated stability at 32.5° C. for 6 months (SVI-STB preparation).

From the FACS analysis, there are no substantial differences between the two independent preparations of Lot 1 and Lot 2 in terms of internalization kinetics of CD26.

The preparation of SVI-STB, a sample of begelomab degraded by incubation at 32.5° C. for 6 months, on the contrary, appears to be less effective than the others in inducing CD26 internalization (FIG. 7). This result supports the capacity of the method of intercepting altered begelomab samples.

As can be seen in the graph in FIG. 7, the eight concentrations of begelomab selected show a high variability in the central region of the curve of a sample of begelomab stored at 4° C. and the sample of begelomab which underwent a thermal excursion to 32.5° C. for prolonged times.

The two samples of begelomab, both stored under optimal conditions at 4° C., show no variability in the central region of the curve.

Potency Evaluation with Different Flow Cytometers

In order to be sure that the results obtained for the internalization of CD26 after incubation with anti-C26 could also be reproduced by changing the reading technology, we conducted the internalization experiments using two cytofluorimeters of different manufacturers.

The results obtained (FIG. 8) clearly demonstrate that the technology belonging to different cytofluorimeters does not alter the results of the internalization curves.

Specifically, in both experiments the sample of begelomab that was preserved under non-optimal conditions (SVI-STB) can be easily identified, showing a high variability in the central part of the curve when compared to the curve of the other 2 Begelomab samples stored under optimal conditions.

Conclusions

The experimental tests carried out demonstrated, through the use of the Karpas 299 cell line, that a cellular assay based on the internalization of CD26 of begelomab-induced membrane has all the characteristics for covering the batch release test function of a drug for clinical use.

In particular, the test based on the internalization of CD26 following the incubation of begelomab allows any possible deviations in the characteristics of the drug released for clinical use to be identified in a specific and reproducible way.

EXAMPLE 3: VALIDATION OF THE POTENCY ASSAY WITH OTHER ANTI-CD26 ANTIBODIES

The potency assay was tested with two other anti-CD26 antibodies:

mouse anti-hCD26-mAb, (Clone 202.36) Thermo Fisher Code: MA1-35147; Lot: 311030F IgG2b, Mouse Isotype K (Clone MG2b-57) BioLegend Code: M1395 as a negative control.

For the detection of CD26 in the membrane, the mouse anti-human CD26 antibody conjugated with APC (Clone M-A261) BD Pharmingen. Code: 563670; Lotto: 8116645, was used.

FIGS. 9 and 10 show the relative potency observed with respect to begelomab (WS-BEG-013). From the results obtained the antibody clone 202.36 shows a relative potency of about 0.01 whereas the antibody clone MG2b-57 shows a complete absence of activity. As can be observed, the potency test according to the present invention is therefore also applicable to other CD26 ligands.

Again in FIG. 9, on comparing the internalization of CD26 with a concentration close to reaching the asymptote for the reference compound WS-BEG-013 (2 μg/mL), a maximum internalization of CD26 greater than 30% is observed only for WS-BEG-013 (32.5%), whereas for the antibody specifically tested the Clone 202.36 is much lower than 20% (11.5%), confirming, according to the criteria declared, that it is an antibody with low potency, i.e. <20% (that is <50% of the plateau %)

FIG. 11 illustrates the potency value of the tested sample (TEST) calculated with respect to the reference standard (RS), to show how the relative activity can be measured quantitatively compared to begelomab. In this case, the reference standard (RS) is begelomab at the concentration of 1.8 mg/mL, whereas the TEST sample is begelomab at a concentration of 1.26 mg/mL, that is 70% of the RS concentration, with an expected relative potency to RS equal to the concentration ratio TEST/RS (e.g. 1.26/1.8=0.7, that is 70%). In FIG. 11 it is demonstrated how at a concentration ratio of 70%, a relative potency of 70% is observed as expected (calculation carried out according to the guidelines USP 1034 "Analysis of Biological Assays" mediante software PLA 3.0).

In the graph of FIG. 11, the MFI value 170 represents the maximum expression value of the membrane CD26 (maximum horizontal asymptote) whereas the value 110 represents the MFI value at which the maximum internalization of CD26 is reached, therefore the value corresponding to the minimum membrane expression (minimum horizontal asymptote). Within this range, defined in absolute value in each assay, potency estimates are carried out by measuring the relative distance of the test curve from the begelomab reference curve.

The histograms shown in the graph show the internalization percentage of CD26 with respect to its maximum membrane expression, represented by the maximum MFI value measured (170). This percentage, when referring to the Test compound, is related to the relative potency:

- at the MFI value 130, RS internalizes 23.1% of the CD26 present in the membrane compared to the Test which only internalizes 18.5% (Test/Reference ratio=0.80);
- at the MFI value 110 (minimum presence of the membrane CD26), RS internalizes 12.1% of the CD26 present in the membrane compared to the Test which internalizes only 9.9% (Test/Reference ratio=0.82).

It can be observed that the potency value is not simply a ratio of internalization percentages at one point, but is calculated as the relative ratio between the two $EC_{50}$s, 0.04342 μg/mL for the Reference and 0.06644 μg/mL for the Test, respectively. The potency calculated in the example in question can, in fact, be estimated as $EC_{50\ RS}/EC_{50\ Test}$ obtaining a value equal to 0.65, i.e. being able to affirm that the potency of the Test is about 70% of the potency of the RS.

Furthermore, by comparing the internalization of CD26 at a concentration close to reaching the minimum horizontal asymptote for the RS (2 μg/mL), a maximum internalization of CD26 higher than 30% is observed for both RS (36%) and for Test (35.9%), confirming, according to the criteria declared, that in both cases it is a high potency, i.e. >30%.

BIBLIOGRAPHY

Abbott C. A., Baker E., Sutherland G. R., McCaughan G. W. Immunogenetics 1994 40: 331-338.

Cordero O J, Yang C P, Bell E B. Immunobiology 2007, 212:85-94.

Morimoto C., Torimoto Y., Levinson G., Rudd C. E., Schrieber M., Dang N. H., Letvin N. L. J. Immunol. 1989, 143: 3430-3439.

Mattern T., Scholz W., Feller A. C, Flad H.-D., Ulme, A. J. Scand. J. Immunol. 1991, 33:737-48.

Gorrel M. D., Gysbers V., Mccaughan G. W. Scand. J. Immunol. 2001, 54: 249-264.

De Meester I., Korom S., Van Damme J., Scharpe'S. Immunol. Today 1999, 20:367-375.

Hildebrandt M., Reutter W., Arck P., Rose M., Klapp B. F. Clin. Sci. 2000, 99:93-104.

Franco R., Valenzuela A., Lluis C., Blanco J Immunol. Rev. 1998, 161:27-42.

Sauer A. V., Brigida I., Carriglio N., Aiuti A. Front Immunol. 2012, 3: 265.

Morimoto C., Schlossman S. F. Immunol. Rev. 1998, 161: 55-70.

Klemann C., Wagner L., Stephan M., von Horsten S. Clin Exp Immunol. 2016, 185(1):1-21.

Ohnuma K., Hosono O., Dang N H., Morimoto C. Adv Clin Chem. 2011, 53:51-84.

Ferrara J L M, Levine J E, Reddy P and Holler E. Lancet 2009, 373:1550-1561.

Welniak L A, Blazar B R and Murphy W J. Annu Rev Immunol 2007, 25:139-170.

Henden A. S., Hill G. R. J Immunol 2015; 194:4604-4612.

Yi T., Chen Y., Wang L., Du G., Huang D., Zhao D., Johnston H., Young J., Todorov I., Umetsu D. T., Chen L., Iwakura Y., Kandeel F., Forman S., Zeng D. Blood. 2009, 114(14):3101-12.

Hatano R., Ohnuma K., Yamamoto J., Dang N. H., Yamada T., Morimoto C. Br J Haematol. 2013, 162(2):263-77.

Bacigalupo A., Deeg J., Caballero D., Gualandi F., Raiola A. M., Varaldo R., Di Grazia C., Van Lint M. T. Abstract 671. ASH Meeting December 2016.

Brevetto U.S. Pat. No. 9,376,498.

Shaikh P. Z. Int. J. of Pharm. & Life Sci. (IJPLS) 2011, 2(11):1247-1263.

Vacaflores, A., Chapman, N. M., Harty, J. T., Richer, M. J., & Houtman, J. C. PLoS One. 2016, 9; 11(6):e0157175.

Seidel U. J. E., SchlegelP., Lang P. Front Immunol. 2013, 4: 76.

The invention claimed is:

1. A method for the in vitro determination of the potency of an anti-CD26 ligand comprising the following steps:
   a) incubating at 37° C. or at room temperature a population of human T lymphocytes expressing the CD26 receptor in a percentage higher than 75% with an anti-CD26 ligand at a concentration ranging from 0.001 µg/ml to 150 µg/ml;
   b) contacting said human T lymphocytes with an anti-CD26 antibody conjugated to a fluorochrome; wherein the anti-CD26 antibody recognizes a different CD26 epitope from the epitope recognized by the anti-CD26 ligand used in step a);
   c) determining the mean fluorescence intensity (MFI) of CD26 measured for the sample of cells treated with the anti-CD26 ligand ($MFI_T$) and the MFI value of untreated cells ($MFI_{NT}$) by means of cytofluorimetric analysis;
   d) evaluating the internalization percentage of the CD26 receptor (% int CD26) or RFI calculated according to the following formula:

$$\% \text{ int } CD26 = 100 - \left(\frac{MFI_T}{MFI_{NT}} \times 100\right)$$

wherein if the value of % intCD26 is:
   less than 20% it indicates a low potency of the anti-CD26 ligand;
   ranging from 20% to 30% it indicates a medium potency of the anti-CD26 ligand; and
   higher than 30% indicates a high potency of the anti-CD26 ligand.

2. The method according to claim 1, wherein said concentration of the anti-CD26 ligand of step a) ranges from 0.01 µg/ml to 100 µg/ml.

3. The method according to claim 1, wherein said fluorochrome of step b) is selected from the group consisting of fluorescein isothiocyanate (FITC), allophycocyanin (APC), phycoerythrin (PE), PE-Cy7, APC-H7, peridinin-chlorophyll-protein (PerCP) and PE-Cy5.5.

4. The method according to claim 1, wherein the population of human CD26+ T lymphocytes of step a) is selected from a population of primary T lymphocytes and a tumoral cell line of human T lymphocytes.

5. The method according to claim 4, wherein said tumoral cell line of human T lymphocytes is the Karpas 299 cell line.

6. The method according to claim 1, wherein the cytofluorimetric analysis of step c) is carried out by fluorescence-activated cell sorting (FACS).

7. The method according to claim 1, further comprising assaying for the inhibition of inflammatory cytokine production; wherein the inflammatory cytokines are selected from the group consisting of IL-8, IL-β3, IL-6, IL-2, GM-CSF, IL-6 and TNF-α; and wherein the assay is performed on the population of human CD26+T lymphocytes of step a).

8. The method according to claim 7, wherein said inhibition of the production of cytokines is evaluated by the MesoScale Discovery assay.

9. The method according to claim 7, wherein said population of human CD26+T lymphocytes is the Karpas 299 cell line.

10. The method according to claim 2, wherein the concentration of anti-CD26 ligand is from 0.01 µg/ml to 2 µg/ml.

11. The method according to claim 2, wherein the concentration of anti-CD26 ligand is from 0.01 µg/ml to 0.5 µg/ml.

12. The method according to claim 3, wherein the fluorochrome is APC.

* * * * *